United States Patent [19]

Conti et al.

[11] 4,425,922

[45] Jan. 17, 1984

[54] ELECTRICAL METHOD AND APPARATUS FOR NON-INVASIVELY DETECTING ABNORMAL FLOW IN CONDUITS

[75] Inventors: James C. Conti; Elaine Strope, both of East Northport; Eugene Findl, Amityville; Cynthia Griffiths, Port Jefferson Station, all of N.Y.

[73] Assignee: BioResearch Inc., Farmingdale, N.Y.

[21] Appl. No.: 251,743

[22] Filed: Apr. 7, 1981

[51] Int. Cl.³ ............................................ A61B 5/02
[52] U.S. Cl. .................................. 128/691; 128/696; 128/700
[58] Field of Search ............... 128/691, 693, 713, 700, 128/695, 696

[56] References Cited

U.S. PATENT DOCUMENTS 3,734,086  5/1973  Phelps ............................ 128/700 X
4,166,455  9/1979  Findl et al. ......................... 128/691

OTHER PUBLICATIONS

Ray, Medical Engineering, Year Book Medical Publishers, Chicago, 1974, pp. 924–925.

*Primary Examiner*—Kyle L. Howell
*Assistant Examiner*—John E. Hanley
*Attorney, Agent, or Firm*—Larson and Taylor

[57] ABSTRACT

Method and apparatus are disclosed for obtaining flow information of a conductive fluid by detecting the streaming potential and analyzing the resultant signal. In a particular embodiment for detecting abnormal blood velocities in the arterial tree, the apparatus includes a flexible sensor having two fixedly spaced apart electrodes and a common mode signal electrode. Each sensor electrode is connected to an input of a differential amplifier and the common electrode is connected to the common input of the differential amplifier. The output signal from the differential amplifier, after filtering and amplification is provided to a recorder or oscilloscope so that it can be compared with the normal or average signal.

A particular embodiment of the method is used to detect blood flow abnormalities, either too fast or too slow compared with most healthy individuals of the same age. In this method, a flexible sensor having two fixedly mounted electrodes is placed on the skin over the artery to be examined, for example the dorsalis pedis artery, so that each electrode is in electrical contact with a different part of the artery. The detected signal is processed and is compared to normal signals. These comparisons can be the wave shape or the time difference between the detection of the wave pulse and a pump timing signal such as the ECG signal.

8 Claims, 9 Drawing Figures

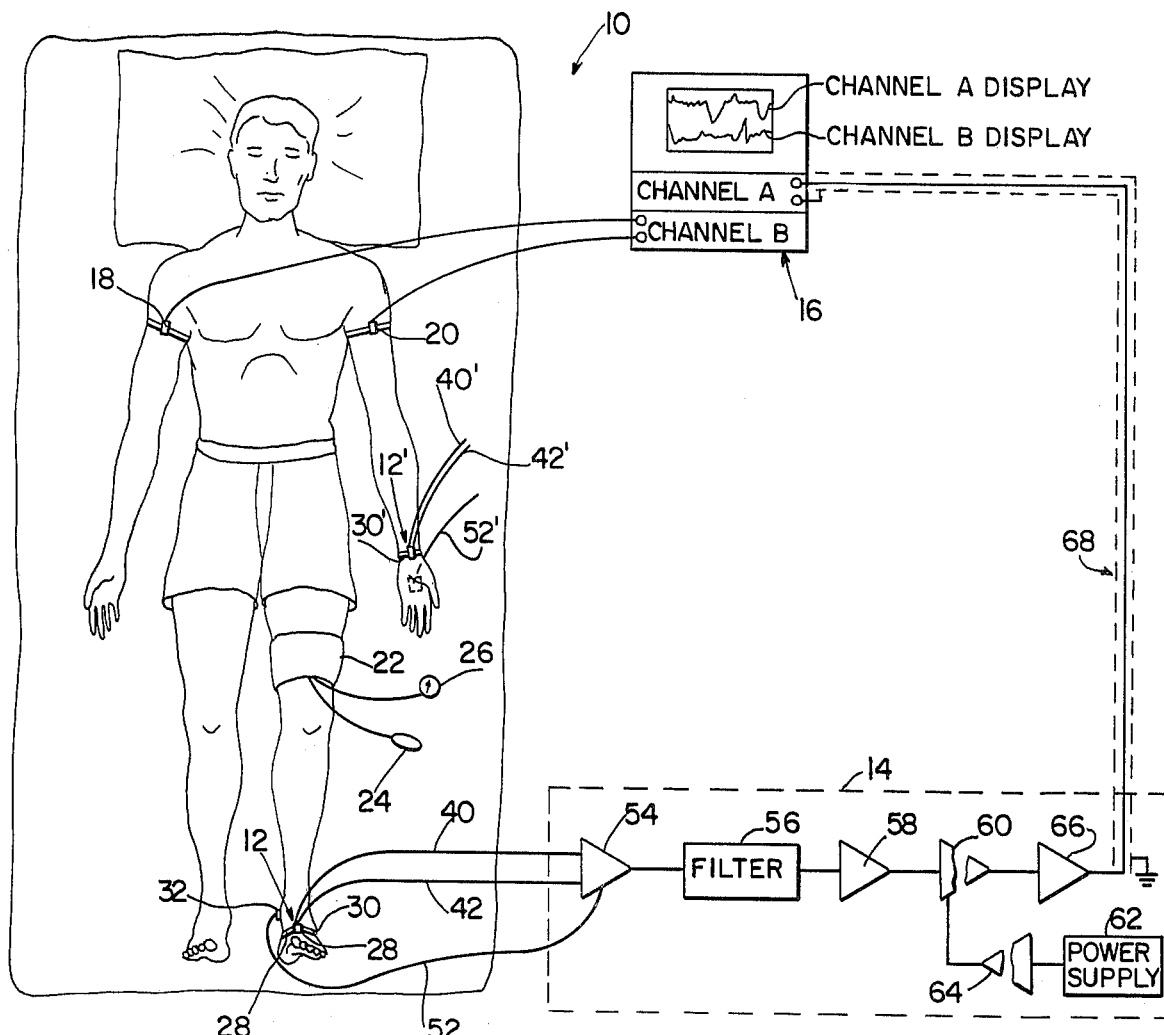
FIG. 1
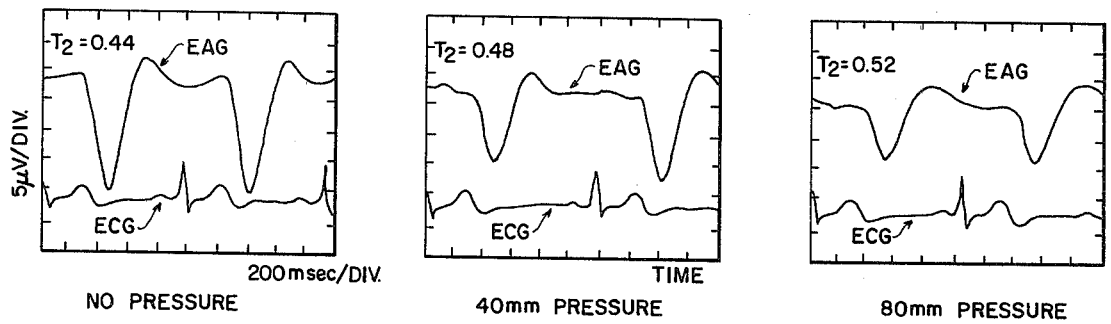
FIG. 1a  NO PRESSURE
FIG. 1b  40mm PRESSURE
FIG. 1c  80mm PRESSURE

ELECTRICAL METHOD AND APPARATUS FOR NON-INVASIVELY DETECTING ABNORMAL FLOW IN CONDUITS

FIELD OF THE INVENTION

The present invention relates to obtaining flow information of a conductive fluid in a conduit. More particularly, the present invention relates to using passively detected electrical voltage generated by a pulsating liquid flow, known as streaming potentials, to obtain velocity information. In one particular adaptation, the present invention provides a means for determining the presence of abnormal blood flow between the heart and the particular artery being investigated.

BACKGROUND OF THE INVENTION

There has been a lot of recent activtity in the non-invasive study of the cardiovascular system. Traditional methods, such as angiography, usually relied on some invasion into the blood vessels. A disadvantage of invasive techniques is the risk of infection, increased mortality risks and increased morbidity risks. For example, there is a one to five percent mortality rate from angiography. Furthermore, those surviving patients often have traumatic reactions to the injected dye. In particular, increased attention has been focused on obtaining a diagnostic indicator of flow problems throughout the arterial tree. Unfortunately, most methods presently in use have significant detractions. One method recently gaining popularity is the use of ultrasound Doppler velocity meters. This process is described in articles such as the ones by Max Anliker, "Diagnostic Analysis of Arterial Flow Pulses In Man;" Cardiovascular System Dynamics, Beran et al, Eds. (1978) and Gosling and King, "Continuous Wave Ultrasound As An Alternative and Complement To X-rays In Vascular Examinations;" Cardiovascular Applications Of Ultrasound, R. Reneman Ed. (1974). The principal drawbacks in using ultrasound are the complex equipment that is needed, the trained technicians and diagnosticians that are required, the complexity of the procedure and the propensity for error based on incorrect vessel diameter and incorrect relative flow directions, and the inability to use the method as a quick screening test to determine potential problems.

Another approach in the investigation of arterial flow is disclosed in the Findl et al. U.S. Pat. No. 4,166,455. This patent disclosed the theoretical basis for using the electrokinetic phenomenon known as streaming potential to determine reduced flow. That patent, which is incorporated in its entirety herein by reference, discloses a method and a sensor for detecting electrical voltages measured on the skin surface. While that method is satisfactory for locating certain lesions located in arteries near the skin surface, it does not provide a method for overall screening purposes to determine whether there is abnormal flow in the arterial tree.

None of the prior art methods and apparatuses provide a simple, inexpensive screening technique for monitoring the changes in blood flow caused by disease stages, traumatic injuries and other factors. Thus, there is the need for inexpensive, uncomplicated, and easy to use apparatus for rapidly screening individuals to detect problems in the cardiovascular system.

SUMMARY OF THE INVENTION

The present invention provides a simple, non-invasive technique and apparatus for obtaining flow information about a conductive fluid flowing in a pulsatile manner through a conduit. Although any types of conductive fluids can be monitored, such as sea water, dissolved chemicals, reactants in chemical processes, and the like, one presently preferred use of the present invention is for detecting cardiovascular problems in animals, and in particular in human beings. The present invention provides a simple, inexpensive technique and apparatus for monitoring, measuring, and analyzing pertinent hemodynamic information. Abnormal blood velocity caused, for example, by lesions and arteriosclerosis located between the heart the the sampling portion or between two sampling points can quickly and easily be determined.

The present invention is based upon the scientific concept of the electrokinetic phenomenon known as streaming potential. This phenomenon can be explained on the basis of Helmholtz' theory of an electrochemical double layer at all liquid-solid interfaces. The streaming potential phenomenon is believed to result by the mechanical perturbation that occurs when the solid, such as the walls of a conduit, is stationary and the liquid is moving. It appears that the fluid flow past the solid interface shears the mobile portion of the double layer in such a way that the predominant ions in the region are displaced in the direction of flow. It is this ion displacement that results in the streaming potential. In a fluid system in which there is pulsatile flow, the flow pulses originate at the pulsatile pump and are transmitted throughout the fluid system. The streaming potential related to the pulse of fluid that is pumped can be measured throughout the entire conduit system. In general, the magnitude of the streaming potential varies with the length of the conduit between the electrodes, with the dielectric constant and the zeta potential, and with the fluid velocity; and varies inversely with the conduit diameter and the electrolyte conductivity. The degree of variation of the streaming potential with each of the variables also depends upon whether the flow is laminar or turbulent.

A particular embodiment of the present invention is connected with blood flow through the arterial tree. As an exemplary only embodiment of the present invention, the present invention will be discussed in this patent application with respect to blood flow in animals.

The streaming potential measurements of animals were reported at least as early as 1975 by Sawyer et al, Coronary Artery Medicine and Surgery—Concepts and Controversies. This investigation utilized electrodes directly placed in contact with the blood flowing in the femoral arteries of dogs and used the streaming potential to determine the zeta potential of the arteries. However, such electrodes when experiencing flow at their surfaces do not accurately measure streaming potentials because of another electrokinetic phenomenon known as the motoelectric potential effect. This artifact is generally of the same order of magnitude as the streaming potential. Although measurements from the surface of the vessel are more difficult to obtain, they are more accurate and reproducible. One such result of that observation was the subject of the aforementioned Findl et al U.S. Pat. No. 4,166,455. That patent discussed the fact that the streaming potential increased when the electrodes straddled the site of a partial flow blockage at least for the reasons that the flow at the location was faster and perhaps because the flow was also turbulent.

On the other hand, the present invention provides a technique for monitoring blood velocity with one application being a rapid method for detecting blockages between the heart and the location of the monitoring electrodes. Although the present invention does not give the exact location of the blockage, it does have the advantage of being a rapid, easy, and inexpensive method of screening for the existence and approximate location of such a partial blockage.

Peripheral vascular diseases result in modifications of blood flow characteristics that can give an indication of the presence of these diseases. By detecting the streaming potential at various locations in the peripheral blood flow, the present procedure being denoted electroarteriography (EAG), rather subtle changes in the peripheral blood velocity profile can be detected. In arteriosclerosis (hardening of the arteries), the pressure pulse from the heart actually travels faster than it does in healthy individuals. In healthy individuals, the artery wall is pliable which results in a slower pressure pulse. In atherosclerosis (lesions in the arteries) the pressure pulse from the heart is slowed by the blockage. Under presently accepted theory, the contracting heart by forcing a pulse of blood into the arterial tree, generates a pressure pulse that causes the blood nearest the artery wall to begin flowing first. This flow generates streaming potentials that can be detected to provide the most accurate velocity waveform.

A particular aspect of the present invention relates to a passive method for detecting the presence of abnormal flow of a conductive fluid in a conduit downstream from a pulsatile pumping source. The method comprises placing first and second, spaced apart, passive electrodes in electrical contact with respective portions of the conduit downstream from the pumping source, detecting the resultant electrical signal, and comparing a characteristic of the signal with a similarly detected signal from a conduit having normal flow.

The apparatus according to another aspect of the present invention provides a means for non-invasively detecting abnormal blood flow downstream of the heart of an animal. The apparatus comprises means for detecting the streaming potential and producing a signal in response thereto, means for detecting the ECG signal; and means for permitting simultaneous comparison of the streaming potential and the ECG signal.

A further apparatus embodiment of the present invention, also capable of being used for non-medical purposes, comprises a differential amplifier means, first and second passive electrodes connected to two inputs of the differential amplifier, and a third passive electrode for providing a common mode rejection signal to the "ground" or "common" connection of the differential amplifier. Further electrode means are provided for detecting a pumping signal from a pulsatile pump that is generated at the beginning of the pumping of a pulse of fluid. There is also provided means for permitting simultaneous comparison of the differential amplifier output signal and of the pumping signal.

These and other objects and advantages of the present invention will be discussed in or become apparent from the detailed description of the presently preferred embodiment contained hereinbelow.

BRIEF DESCRIPTION OF THE DRAWINGS

FIG. 1 is a schematic diagram depicting the figure of a human being with electrode placement combined with an electrical schematic of a particular embodiment of the present invention.

FIGS. 1a, 1b, and 1c are reproductions of sample signals obtained using the method of the present invention at the indicated cuff pressures.

DETAILED DESCRIPTION OF THE PREFERRED EMBODIMENTS

Figure 2:
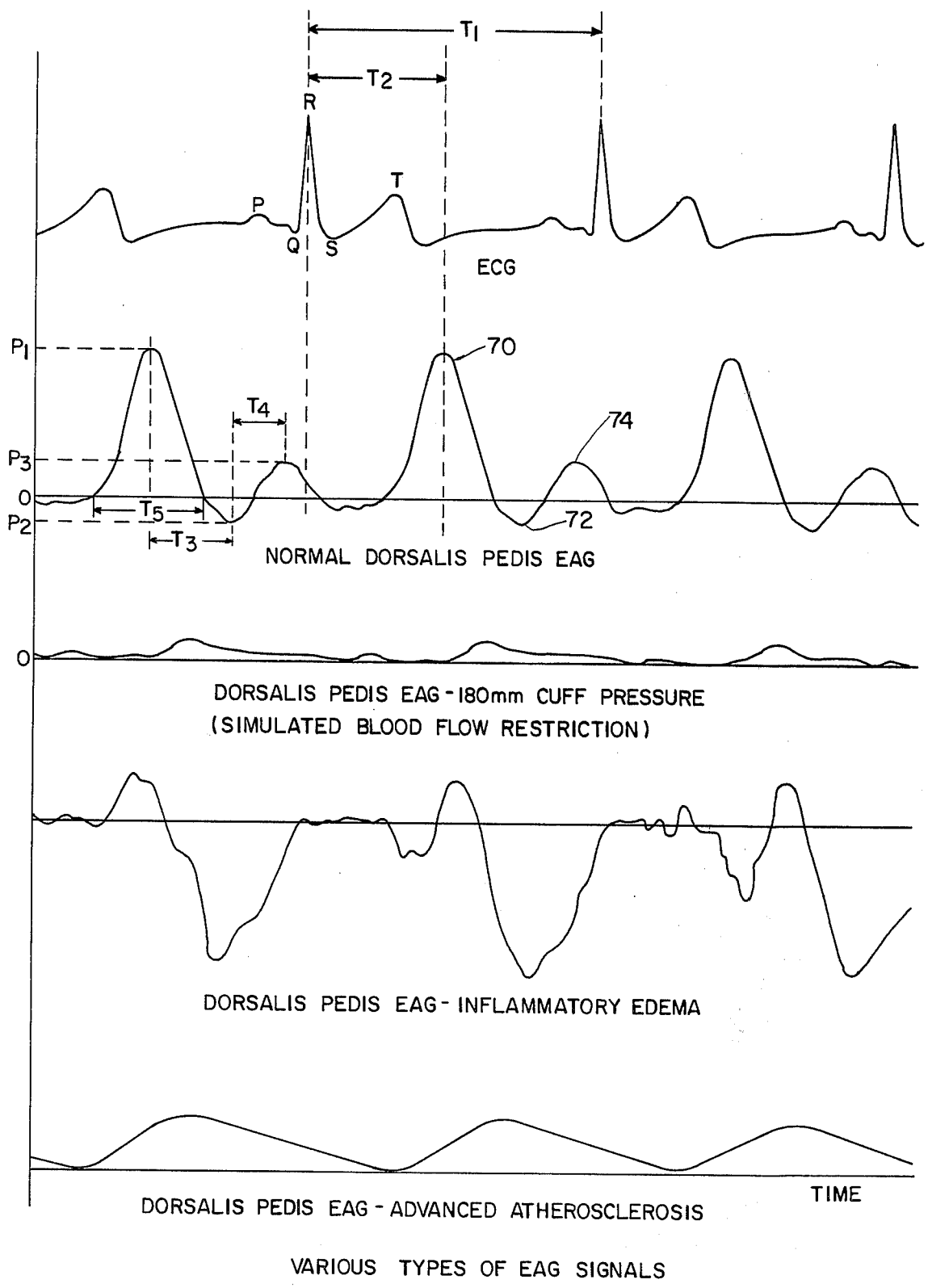
FIG. 2 is a graphical portrayal of a typical electrocardiogram and several electroarteriograms of different types of peripheral arterial blood flow.

Referring now to the drawings in which like elements are represented by like numerals throughout the several views, and in particular with reference to FIG. 1, the electroarteriography (EAG) apparatus 10 is depicted. EAG apparatus 10 comprises an EAG sensor 12, an electronic processing circuit 14, and a signal analyzing means such as oscilloscope 16. EAG apparatus 10 is shown connected to a test subject shown in the prone position. Attached to each arm of the subject are conventional electrocardiogram (ECG) electrodes 18 and 20. A conventional, air inflatable cuff 22, such as those used for taking blood pressure, is shown placed between the location of EAG sensor 12 and the patient's heart. Cuff 22 has a conventional, air inflating device such as a rubber bulb 24 and an indicating pressure gauge 26. Thus, when cuff 22 is inflated by repeatedly compressing and releasing bulb 24, the amount of pressure can be read on gauge 26. Obviously, as cuff 22 is inflated to a higher and higher pressure, the amount of blood flow on the distal side of cuff 22 from the heart will decrease. At pressures above systolic, an inflation pressure of approximately 150 millimeters of mercury, a complete cut-off of the blood flow beyond cuff 22 occurs and the EAG signal disappears.

EAG sensor 12 is depicted in FIG. 1 as being connected for measurement of blood flowing through the dorsalis pedis artery. Also shown in FIG. 1 at 12' is an alternate EAG sensor site to measure the blood flowing through the radial artery. Other locations for the EAG sensor can include the neck for monitoring the carotid artery; on the inside, lower side of the foot to monitor the posterior tibial artery; on the inside of the elbow to monitor the brachial artery; and on the anterior inner part of the thigh to monitor the femoral artery. The precise EAG sensor locations are illustrative only and are not meant to be either all inclusive or to be limiting. The EAG signal, described in greater detail hereinbelow, will vary in both the shape of the signal and the magnitude of the signal depending upon the particular location of EAG sensor 12. For illustrative purposes, the results of the EAG signal taken from the dorsalis pedis artery will be discussed and compared for various physiological conditions in the remainder of this application.

Figure 3:
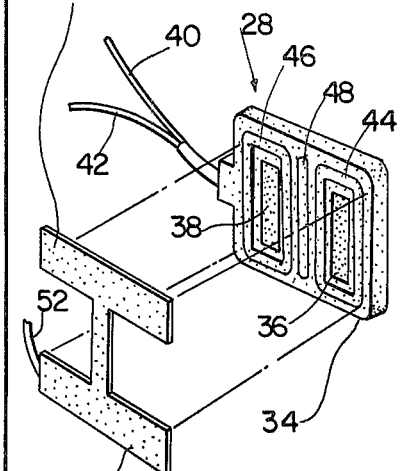
FIG. 3 is a perspective view of one embodiment of the electrodes of the present invention.

EAG sensor 12 comprises an EAG electrode or pad 28, a means for attaching pad 28 to the body, such as an adjustable band 30, and a common mode signal electrode 32. With reference to FIG. 3, EAG pad 28 is comprised of a body 34, two electrode pads 36 and 38 housed in cavities in body 34, and silver wires 40 and 42 respectively adhered to the back of electrode pads 36 and 38. Body 34 is preferably flexible to conform with the shape of the subject and is non-conductive. For example, body 34 can be molded from RTV or silicone rubber and have exemplary dimensions of 230 square millimeters. Electrode pads 36 and 38 are preferably molded from flexible silver filled silicone rubber and are located relatively closely to each other. Electrode pads 36 and 38 have exemplary dimensions of 3 millimeters by 14 millimeters and can be spaced apart from 6 millimeters to 15 millimeters on center with a presently preferred spacing of 10 millimeters. Electrode pads 36 and 38 are located in cavities in body 34 and extend below the outer surface thereof. The space above the tops of electrode pads 36 and 38 is filled with a conventional electrode jelly 50.

Figure 5:
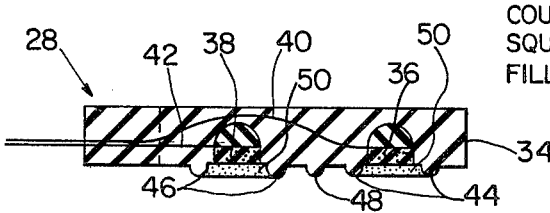
FIG. 5 is a cross-sectional view taken along line 5—5 of FIG. 4.

As clearly shown in FIG. 5, the inside surface of EAG pad 28, that is the side to be placed on the skin of the subject, has a plurality of isolation ridges to assure electrical isolation between electrode pads 36 and 38. Annular ridges 44 and 46 (see also FIG. 3) surround electrode pads 36 and 38, respectively, and an elongate ridge 48 extending transversely on body 34 between the inward parts of annular ridges 44 and 46 further isolates electrode pads 36 and 38 from each other. Because electrode jelly tends to migrate when heated by the body, ridges 44, 46 and 48 assure that such migration is contained and does not affect the mutual electrical isolation of electrode pads 36 and 38. Thus, EAG pad 28 is completely flexible and reusable and can easily conform to the particular shape of the body portion on which it is applied. Most importantly, EAG pad can be firmly mounted over an artery without occluding the artery. The electrode spacing is fixed to provide consistent results and the electrode size and electrical contact area with the skin is minimal to reduce electrical artifacts.

Figure 4:
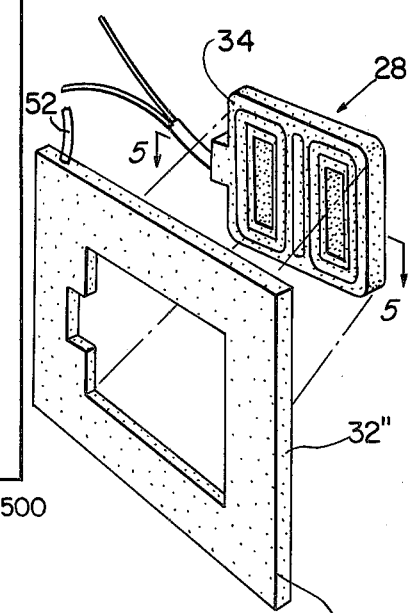
FIG. 4 is a perspective view of a further embodiment of electrodes of the present invention.

Common mode signal electrode 32 can be either a conventional ECG electrode or can be used in combination with EAG pad 28, as shown in FIGS. 3 and 4 and denoted 32' and 32" respectively. Electrode 32' and 32" are silver filled silicone rubber electrodes that have an "H" configuration, and an annular square configuration, respectively. Electrodes 32' and 32" have a size and configuration so as to permit electrode pads 36 and 38 to contact the skin of the subject. Other configurations, such as two parallel strips, can obviously be used. Electrode 32' as depicted in FIG. 3 has a size such that it will be contained within the perimeter of body 34, whereas the electrode 32" as depicted in FIG. 4 has a size such that its annular opening will receive body 34. In both cases, common mode signal electrode 32 is designed to be closely spaced to electrode pads 36 and 38. Alternatively, as depicted in FIG. 1, electrode 32 is placed on the subject at a location that is spaced from EAG pad 28. Such an electrode 32 can be typically placed on a bony area (e.g., the patella or the fibula) to reduce the possibility of electrode 32 sensing an EAG signal. A wire 52 is mounted on electrode 32 and can be easily connected to electronic processing circuit 14.

As shown in FIG. 1, electronic processing circuit 14 includes a front end differential amplifier 54 having at least two signal inputs and a common input. Wires 40 and 42 are electrically connected to the signal inputs of differential amplifier 54 and wire 52 is electrically connected to the common input of differential amplifier 54. Although an ideal differential amplifier will not respond to the common difference between the input signals, a practical differential amplifier will in fact measure a difference between two symmetrical input signals and amplify that difference. The ability of a practical differential amplifier to reject the common signal between the two inputs is denoted the common mode rejection ratio (CMRR). Typical CMRR are $10^6$ which means that a common one volt signal will appear as a microvolt artifact. Because the EAG signal is of the same order of magnitude (e.g. 1 to 2 microvolts), this is a significant error. The common signal to both inputs is usually generated by the omnipresent 60 hertz noise as well as the ECG and EMG signals from the patient. Electrode 32 when placed so as not to measure an EAG signal and when connected to the common connection of differential amplifier 54 greatly enhances the performance of circuit 14. As a result, a hundred fold increase in EAG signal magnitude over the noise level was obtainable.

Differential amplifier 54 can have a common mode rejection ratio of 100 db with a differential impedance of $10^{12}$ ohms, a common mode impedance of $10^{12}$ ohms, and a noise level of 5 microvolts RMS in a frequency range from 10 to 500 hertz. As a result of using the common mode signal electrode 32 connected to the ground connection of differential amplifier 54, the overall common mode rejection of differential amplifier 54 is increased to 150 db.

The output from differential amplifier 54 is fed through a filter 56 and a range select conventional amplifier 58 to a conventional isolation amplifier 60. Filter 56 can be a conventional two pole butterworthy bandpass filter in the 0.5 to 40 hertz band. The power for isolation amplifier 60 is provided from a power supply 62 fed through an isolator 64. In this way, a signal with no ground currents can be obtained. The output from isolation amplifier 60 is connected through an output buffer 66 to the output connection of circuit 14.

As mentioned above, the input signal levels to circuit 14 are typically in the low microvolt range whereas the output signals therefrom are typically in the low millivolt range. Depending upon the setting of amplifier 58, the overall gain of circuit 14 can be 100, 1,000, or 10,000 and, as mentioned above, the overall common mode rejection ratio is 150 db at 60 hertz.

The outut from electronic processing circuit 14 is connected through a grounded coaxial cable 68 to the channel A input of oscilloscope 16. For the purposes of easy comparison, the output of circuit 14 is connected to oscilloscope 16 such that forward flow causes a negative signal. Although an oscilloscope 16 is disclosed in FIG. 1, it should be obvious that the same connections can be made to an ECG recorder or other signal recording or storage devices.

As shown in FIG. 1, the performing of the method according to the present invention in the embodiment of electroarteriography comprises the placement of ECG electrodes on a subject that is prone on a bed or similar platform. Two ECG type electrodes are placed on one arm and one on the other arm. Depending upon the portion of the arterial tree to be screened, the artery of interest is located by either palpation or by use of a conventional sonic detector. The dorsalis pedis artery was selected for EAG pad 28 and the radial artery was selected for EAG pad 28'. Discussing only the signals from the dorsalis pedis artery, EAG pad 38 is placed on the skin of the subject directly over the artery with electrode pad 36 and 38 placed so that it is upstream of the other pad 38 or 36. EAG pad 28 is held in place by an appropriate means such as an adjustable strap or band 30 that is attached so as not to occlude the artery. Common mode signal electrode 32 is then attached over a bony portion of the foot of the subject and all three electrodes are connected, as discussed above, to circuit 14. Circuit 14 is then connected to the channel A input of oscilloscope 16.

FIG. 1a shows the waveform obtained from both the EAG pad 28, at the top of the graph, and the ECG waveform from ECG electrodes 18 and 20 shown at the bottom of the graph. Reference is also made to the top two wave forms in FIG. 2 where the top waveform is the ECG signal and the bottom waveform is an EAG signal that has not been inverted. A typical ECG waveform consists of a series of complex pulses which are believed to be the result of electrical signals sent to stimulate the pumping action of the heart. A typical pumping action from the heart results in a first forward flow of flood through the arteries, a small reversal of that blood flow, and a subsequent forward flow of the blood. The particular blood flow is believed to be correlated with the ECG waveform. As shown in FIG. 2, the ECG complex wave has a small positive segment labelled "P", followed by a small negative part, denoted "Q", which immediately precedes a large spiked pulse denoted "R". The end of the R portion is a small negative portion, denoted "S" which slowly rises to a medium size positive pulse portion, denoted "T". Thus, the standard ECG waveform is comprised of a complex "PQRST" pulse. Because of the regular form of the ECG pulses, they cannot only be used as timing pulses, but they can also be used to trigger an oscilloscope in a known manner. In fact, the FIGS. 1a, 1b, and 1c are reproductions of actual signals obtained from human test subjects in which the oscilloscope was triggered by the R portion of the ECG.

A principal discovery underlying the present invention is that the streaming potential produces a measurable signal having a complex waveform resulting from the forward-backward-forward flow of blood through the arteries. The shape of this waveform and the relative timing of the waveform with respect to the ECG waveform can determine whether the flow through the arteries is normal, is reduced because of some lesion, disease or traumatic injury is the arterial tree between the heart and the location of the EAG electrodes, or is too fast, being indicative of arteriosclerosis.

With particular reference to FIG. 2, a normal dorsalis pedis EAG consists of a first, large positive peak, denoted 70, a second, small negative peak denoted 72, and a small positive peak denoted 74. The time between the R peak of the ECG signal and peak 70 of the EAG signal is denoted the $T_2$ time and is a function of the time delay between the contraction of the heart and the subsequent pulse of blood flowing past the particular EAG electrode. The further the placement of the EAG electrode from the heart, the greater the $T_2$ time. Similarly, the $T_2$ time will be increased if the blood flow is uphill, such as with the leg raised above the heart, than with the blood flow that is downhill, such as in a standing subject. Other time portions of the EAG signal is the time from peak 70 to peak 72, the $T_3$ time, the time from peak 72 to peak 74, the $T_4$ time, and the pulse width of peak 70, the $T_5$ time. The $T_1$ time, shown in the upper graph in FIG. 2, is the time between heartbeats and is measured between the two R peaks of the ECG signal. Other usable characteristics of the EAG signal is the height of peak 70, denoted $P_1$; the height of peak 72, denoted $P_2$; and the height of peak 74, denoted $P_3$. More particularly, it has been found that while the absolute value of the amplitude of these peaks may vary from day to day as a result of artifacts, the ratio of the peak amplitudes apparently remains constant.

In order to simulate the effects of different amounts of restrictions to the blood flow, a blood pressure cuff 22 was placed on the thigh of the subject and inflated to various pressures from 0 through systolic pressure for the individual subject to a cut-off pressure. As mentioned above, FIG. 1a shows the result with no pressure in cuff 22, FIG. 1b shows the results of 40 millimeters (Hg) of pressure in cuff 22, and FIG. 1c shows the result with 80 millimeters (Hg) of pressure in cuff 22. Other studies performed on a subject with a known traumatic injury to the left foot resulting in permanent inflammatory edema confirmed that there is a dramatic difference in the EAG signal obtained from the normal foot than from the pathologic foot. The normal foot contained the typical EAG waveform as shown in FIG. 1a or at the second curve from the top in FIG. 2, whereas the pathological foot had an EAG signal that was very broad, lacking well defined flow reversal, and that began late in the cycle as shown in FIG. 2.

A study of various EAG signals indicates that the signals vary with a number of factors. These factors include the location at which the signal is obtained, the heartbeat of the subject (e.g. taken while the subject is at complete rest or after the subject has walked on a treadmill), and the location and extent of blockage of blood flow. In addition, possibly because of inconsistent electrode placement techniques, the absolute amplitude of the EAG signal may vary from test to test. Reliable modifications of an EAG signal from an average signal that reflect predicted hemodynamic changes include the broadening of the pulse width ($T_5$ greater), lack of flow reversal ($P_2$ equals zero), a decrease in ratios of signal amplitude ($P_2/P_1$), and the length of time between the peak of the ECG QRS wave and the peak of the subsequent EAG wave ($T_2$ time). In addition, possibly because of inconsistent electrode pressures, the absolute amplitude of the EAG wave parts may vary from test to test.

A review of FIG. 1b, 1c and the middle waveform in FIG. 2, shows that with increasing pressure in cuff 22, $P_1$ decreases, pulses 72 and 74 become less defined, and $T_2$ increases. In fact, the middle wave in FIG. 2 is so distorted that it could simply be due to background noise. The bottom two waveforms in FIG. 2 show other effects on the EAG signal from reduced blood flow.

Figure 6:
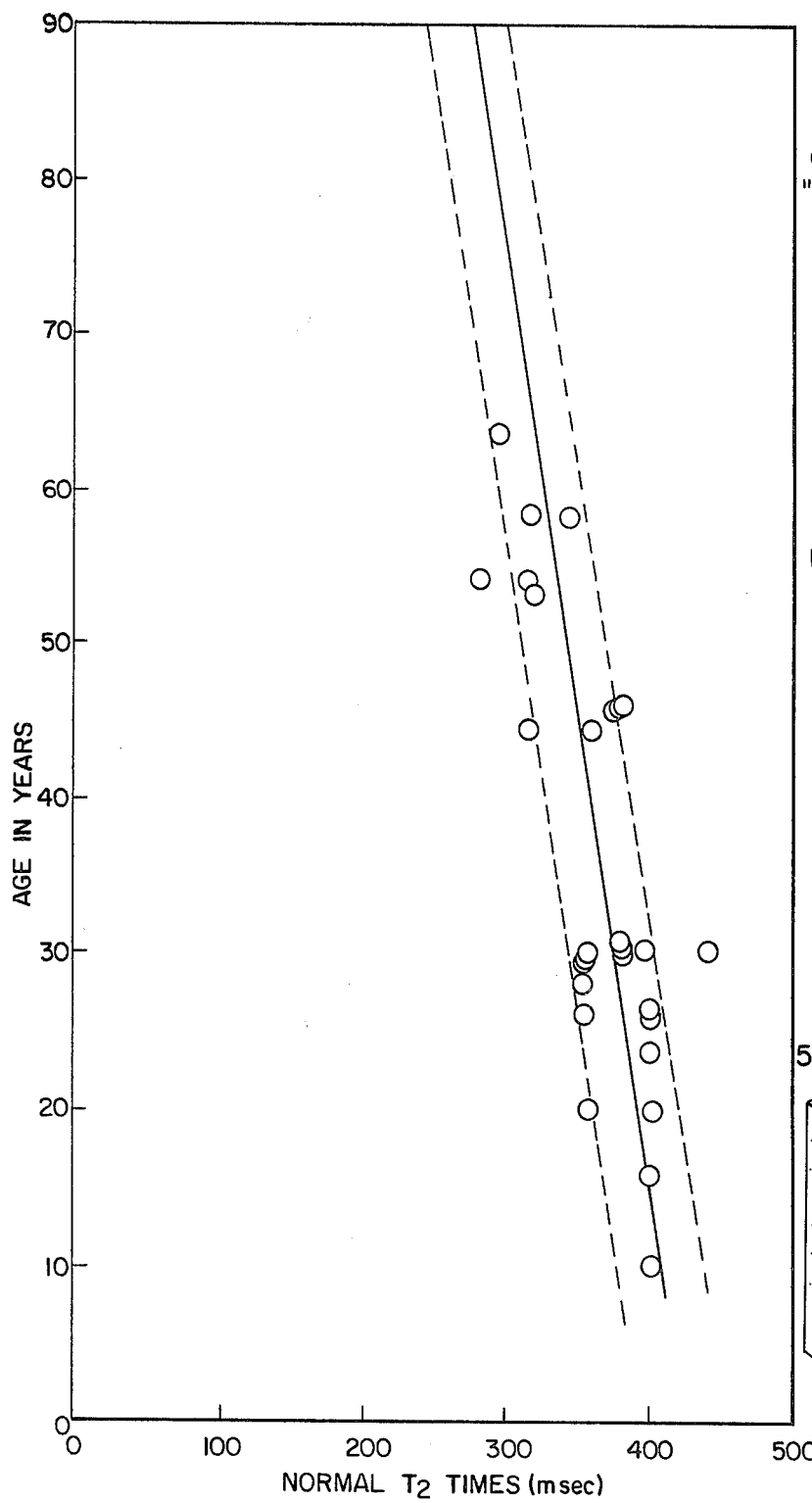
FIG. 6 is a graphical plot of normal $T_2$ times (time between the R pulse of the ECG and the subsequent EAG pulse) plotted as a function of the age of the individual.

With reference now to FIG. 6, the $T_2$ transit times for non-symptomatic "normal" subjects obtained from the dorsalis pedis artery are depicted as falling within a normal band of values shown by the two dashed lines. The $T_2$ times were found to decrease with age and this is believed to be the result of the tendency of arteries to harden with age and the tendency of blood pressure to increase with age. Hardening of the arteries (arteriosclerosis) lowered the transit time by decreasing the ability of the arterial wall to flex, making the artery more like a rigid tube. The lowered wall compliance translates into a faster blood flow and a decreased $T_2$. Not shown in FIG. 6 is the effect of the height of the person, or rather the distance from the heart to the EAG sensor. It has been found that there is an increase in $T_2$ time on the order of 20 to 40 milliseconds for a distance of one foot.

Although there are numerous factors which result in the variation of the $T_2$ time, it has been found that whenever the $T_2$ time falls outside of the "normal" range, (i.e., is too large or too small based on the age of the subject) there is probably an abnormality in the blood velocity and further examination is warranted. Such further examination can be a detailed analysis of the EAG waveform or the use of other means to confirm the presence of atherosclerosis or arteriosclerosis, or some other possible damage to the arterial tree. Two clinical tests shown in Table I below illustrate the utility of the $T_2$ time.

TABLE I

| Patient Info. | | $T_2$ time (msec) | | |
|---|---|---|---|---|
| Age | Sex | R. Leg | L. Leg | Diagnosis |
| 90 | M | 230 | 360 | Atherosclerosis present in left leg. (Confirmed by angiography.) Right leg borderline normal. Arteriosclerosis in excess of normal for age suspected. |
| 68 | M | 780 | 890 | Severe atherosclerosis in both legs. Blood flow seriously reduced. (Confirmed by angiography.) |

From experimental results, 86% of the trials indicated waveforms as depicted in FIGS. 1a, 1b, and 1c. A 10 to 20% increase in $T_2$ time usually accompanied cuff pressures at or below the diastolic pressure of the subject. In fact, a 10 to 20% increase in the $T_2$ time was obtained with an applied cuff pressure of 40 millimeters of mercury. Although the present invention does not necessarily provide a determination of the extent of an occlusion or the exact location of the occlusion, it does provide an easily applied test with immediate results which can be used to determine whether further tests should be done.

Application of the present invention, obviously, can be in the preliminary screening for occlusive cardiovascular disease. Other uses, in a non-medical field could be the monitoring of pulsatile flow of a conductive liquid in chemical experiments, in manufacturing processes, and in liquid transportation systems. In fact, the present invention can be used in any fluid transport system in which there is a possibility of an occlusion in the conduit of the system.

As described above, the present invention provides a screening process requiring no special signal processing and having a high correlation with the actual blood velocity profile and between the transit time through the vessel and the degree of occlusion in the vessel. The present invention utilizes passive electrodes of a very simple construction. By passive electrodes it is meant an electrode that only receives an electrical signal and is not used to transmit either voltage or current to the vessel being monitored. In addition, a passive electrode does not involve a chemical reaction and is substantially unaltered by the monitoring process.

Although one aspect of the present invention utilizing the $T_2$ time as the measured signal characteristic employs the ECG signal, it is obvious that in both animal and non-animal applications of the present invention a separately generated pumping signal can be used or a second set of electrodes can be placed closer to the pump outlet to provide an initial signal to which the distally detected signal can be compared. Non-animal applications require a conduit that is a poor conductor in the axial direction and conductive in the radial direction (e.g., porous glass). No streaming potentials are generated in axially conductive conduits (e.g. metal) and none can be detected non-invasively in radially non-conductive conduits (e.g. plastic).

With respect to the medical applications of the present invention, the present invention provides a reliable, simple and non-invasive blood velocity measurement technique that has substantial value in today's clinical environment. The EAG waveform is remarkably similar to the blood velocity profiles that have been obtained using ultrasound techniques and, as mentioned above, are believed to be more accurate. Because blood is a conductive fluid and because the blood vessel is immersed within a bulk conductor, the streaming potentials from the blood flow through certain arteries can be detected along the skin surface above that artery.

The apparatus according to the present invention provides an effective way of measuring and comparing velocity dependent voltage signals produced by streaming potentials. The use of a common mode signal electrode connected to the common input of a differential amplifier permits the low voltage streaming potentials to be detected among the much larger noise signals.

The above invention has been described in detail with respect to specific embodiments thereof. However, obvious modifications should be apparent to those skilled in the art.

We claim:

1. Apparatus for non-invasively detecting reduced blood flow downstream of the heart comprising:
   means for detecting the streaming potential of an artery and producing a signal in response thereto;
   means for detecting the ECG signal; and
   means for permitting simultaneous analysis of said streaming potential and said ECG signal.

2. Apparatus as claimed in claim 1 wherein said streaming potential detecting means comprises differential amplifier means; a first electrode connected to one input of said differential amplifier means; a second passive electrode connected to a second input of said differential amplifier means; and a third passive electrode for providing a common mode rejection signal connected to the common connection of said differential amplifier means.

3. Apparatus as claimed in claim 2 and further including means for mounting said first and second electrodes closely spaced to each other and on the surface of the animal being monitored above the artery being monitored.

4. Apparatus as claimed in claim 2 wherein said comparison permitting means permits calculation of the time delay between the R peak of the ECG signal and the peak of the streaming potential signal.

5. Apparatus as claimed in claim 2 wherein said comparison permitting means permits visual observation of the waveform of the streaming potential signal.

6. Apparatus as claimed in claim 5 and further including
   a further differential amplifier means;
   a fourth passive electrode connected to one input of said further differential amplifier means;

a fifth passive electrode connected to a second input of said further differential amplifier means;

a sixth passive electrode for providing a common mode rejection signal to the common connection of said further differential amplifier means;

said first, second and third electrodes forming a first set of electrodes for detecting streaming potential and said fourth, fifth and sixth electrodes forming a second set of electrodes for detecting a second streaming potential;

first means for attaching said first, second and third electrodes to one general location of the artery in closely spaced relationship to each other;

second means for attaching said fourth, fifth and sixth electrodes to a second general location of the artery in closely spaced relationship to each other;

and wherein said analysis permitting means further permits analysis of characteristics between the signals detected by said first and second sets of electrodes with characteristics between similar signals obtained from a similar artery used as a reference.

7. A passive method for detecting abnormal flow in the arterial tree of an animal, the method comprising:

placing a first passive electrode in electrical contact with a suspect artery;

placing a second passive electrode in electrical contact with the suspect artery, the second electrode being spaced from the first electrode;

detecting an electrical signal between the electrodes, the electrical signal having a voltage component above and below a base line level for the suspect artery;

similarly detecting a similar electrical signal of a reference artery; and comparing the ratio of the above component to the below component of the detected signal of the suspect artery with the ratio of the above component to the below component of the reference artery.

8. A passive method for detecting abnormal flow in the arterial tree of an animal, the method comprising:

placing a first passive electrode in electrical contact with a suspect artery;

placing a second passive electrode in electrical contact with the suspect artery, the second electrode being spaced from the first electrode;

detecting an electrical signal including a pulse portion;

similarly detecting a similar electrical signal and pulse portion of a reference artery;

detecting a R portion of an ECG signal;

determining a $T_2$ time difference between the R peak and the subsequently detected pulse portion of the electrical signal from the suspect artery and the reference artery; and comparing the two $T_2$ time differences.

* * * * *